US011525837B2

(12) United States Patent
Yamashita et al.

(10) Patent No.: US 11,525,837 B2
(45) Date of Patent: Dec. 13, 2022

(54) AUTOMATIC ANALYZER

(71) Applicant: Hitachi High-Technologies Corporation, Tokyo (JP)

(72) Inventors: Yoshihiro Yamashita, Tokyo (JP); Takenori Okusa, Tokyo (JP); Shunsuke Sasaki, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 387 days.

(21) Appl. No.: 16/637,808

(22) PCT Filed: Jul. 26, 2018

(86) PCT No.: PCT/JP2018/028020
§ 371 (c)(1),
(2) Date: Feb. 10, 2020

(87) PCT Pub. No.: WO2019/087482
PCT Pub. Date: May 9, 2019

(65) Prior Publication Data
US 2021/0018522 A1    Jan. 21, 2021

(30) Foreign Application Priority Data
Nov. 2, 2017   (JP) .............................. JP2017-212407

(51) Int. Cl.
*G01N 35/00*    (2006.01)
*G01N 33/543*   (2006.01)
*G01N 35/02*    (2006.01)

(52) U.S. Cl.
CPC ..... *G01N 35/00584* (2013.01); *G01N 33/543* (2013.01); *G01N 35/0098* (2013.01); *G01N 35/025* (2013.01); *G01N 2035/00356* (2013.01)

(58) Field of Classification Search
CPC .......... G01N 2035/00356; G01N 2035/00445; G01N 2035/0444; G01N 33/543; G01N 35/00584; G01N 35/0098; G01N 35/025
See application file for complete search history.

(56) References Cited

U.S. PATENT DOCUMENTS

| | | | | |
|---|---|---|---|---|
| 5,580,524 A | * | 12/1996 | Forrest | G01N 35/00663 436/174 |
| 2011/0097240 A1 | | 4/2011 | Yamashita et al. | |
| 2015/0007583 A1 | * | 1/2015 | Murata | F25B 21/02 62/3.2 |

FOREIGN PATENT DOCUMENTS

| | | |
|---|---|---|
| EP | 1 475 640 A2 | 11/2004 |
| JP | 10-311834 A | 11/1998 |

(Continued)

OTHER PUBLICATIONS

English translation of JP-5978039-B2 (Year: 2016).*
(Continued)

*Primary Examiner* — Jennifer Wecker
*Assistant Examiner* — Jonathan Bortoli
(74) *Attorney, Agent, or Firm* — Mattingly & Malur, PC

(57) ABSTRACT

An object is to provide an automatic analyzer that prevents an effect of various environmental changes on an equilibrium state of an immunological binding reaction. An automatic analyzer of an embodiment of the invention includes a B/F separation unit that executes a B/F separation step separating an unreacted component and a reacted component from a liquid in which a sample and a reagent are reacted, a detection unit that detects a reacted component in the liquid after the B/F separation step, and a temperature maintaining unit that maintains the B/F separation unit and the detection unit in substantially the same temperature environment.

7 Claims, 3 Drawing Sheets

(56) References Cited

FOREIGN PATENT DOCUMENTS

| | | | |
|---|---|---|---|
| JP | H11316235 | * | 11/1999 |
| JP | 2013-088164 A | | 5/2013 |
| JP | 2013088164 A | * | 5/2013 |
| JP | 5978039 B2 | * | 8/2016 |
| WO | 2009/151058 A1 | | 12/2009 |

OTHER PUBLICATIONS

English translation of JP2013088164A (Year: 2013).*
English translation of JPH11316235 (Year: 1999).*
International Search Report of PCT/JP2018/028020 dated Sep. 25, 2018.
Extended European Search Report received in corresponding European Application No. 18872383.7 dated Jul. 20, 2021.

* cited by examiner

[FIG. 1]
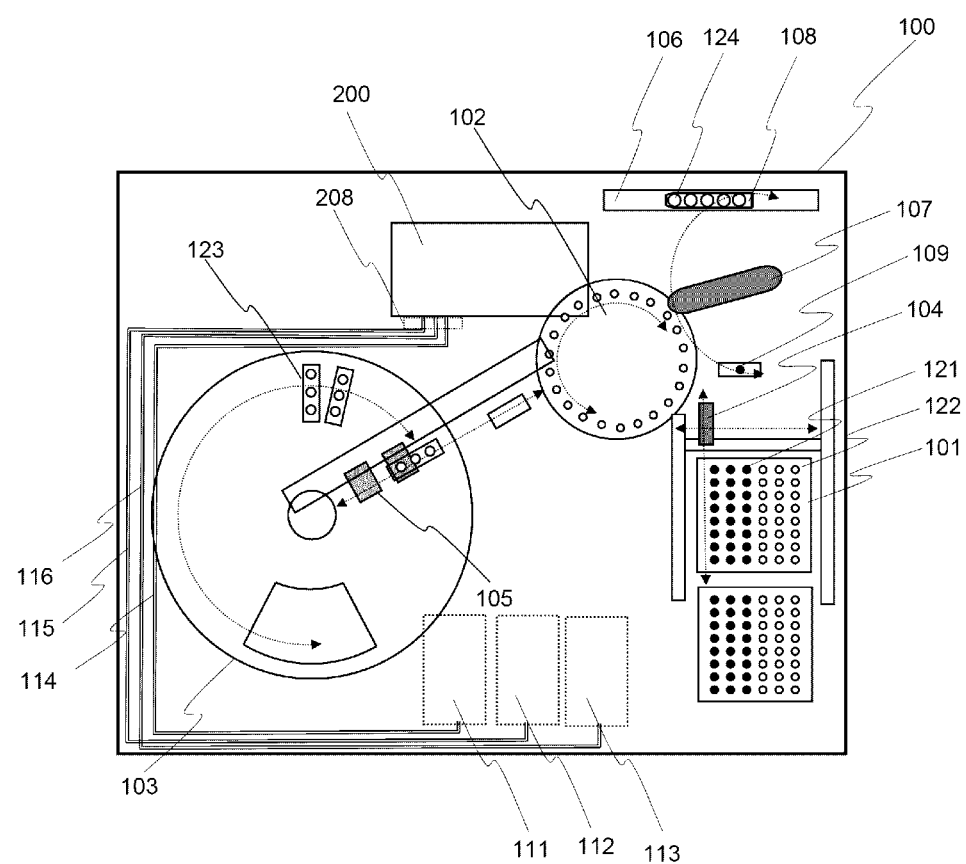

[FIG. 2]
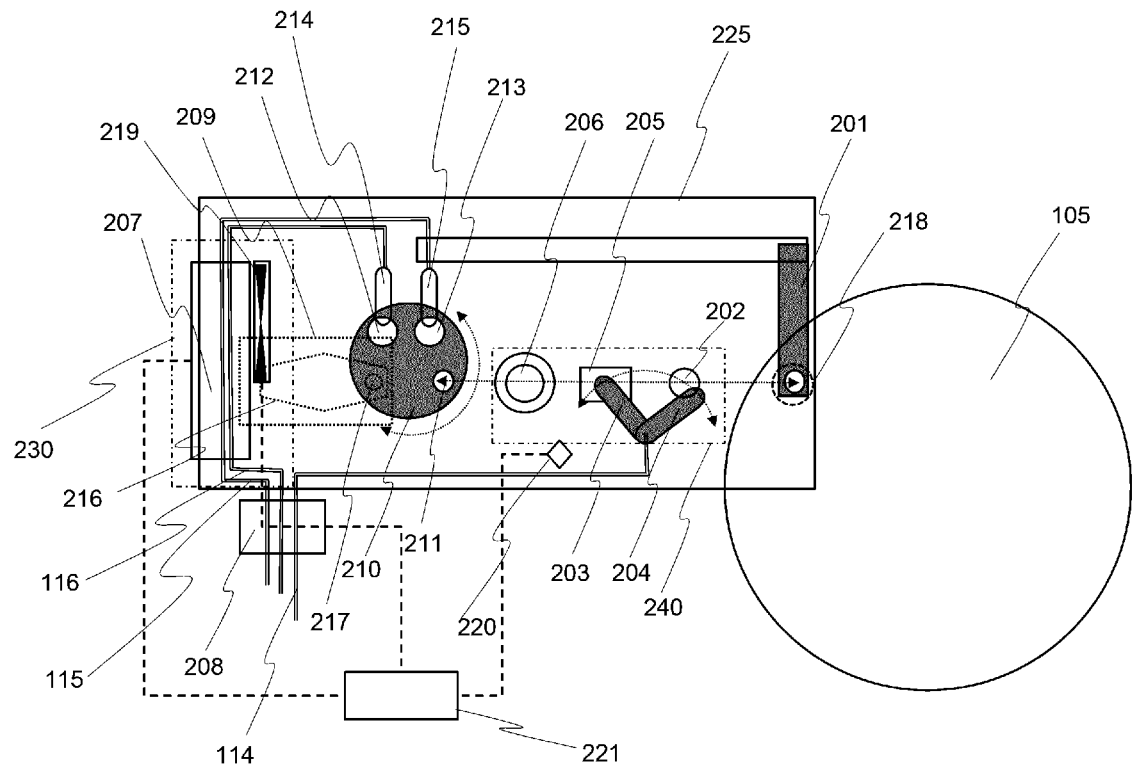
[FIG. 3]
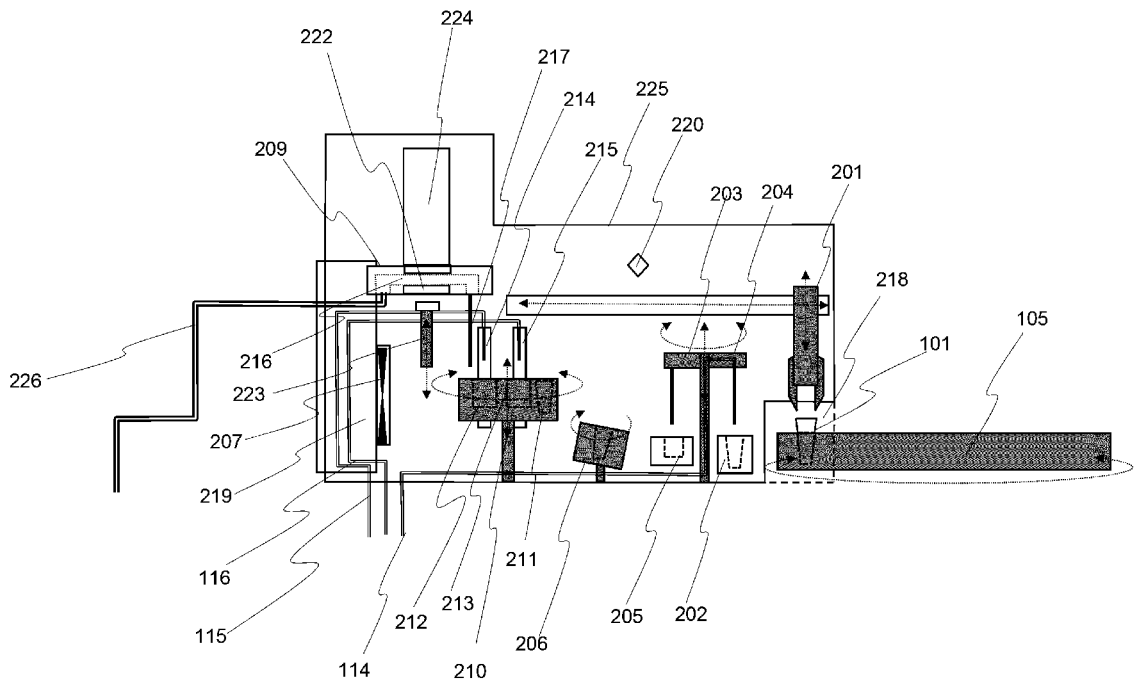

[FIG. 4]
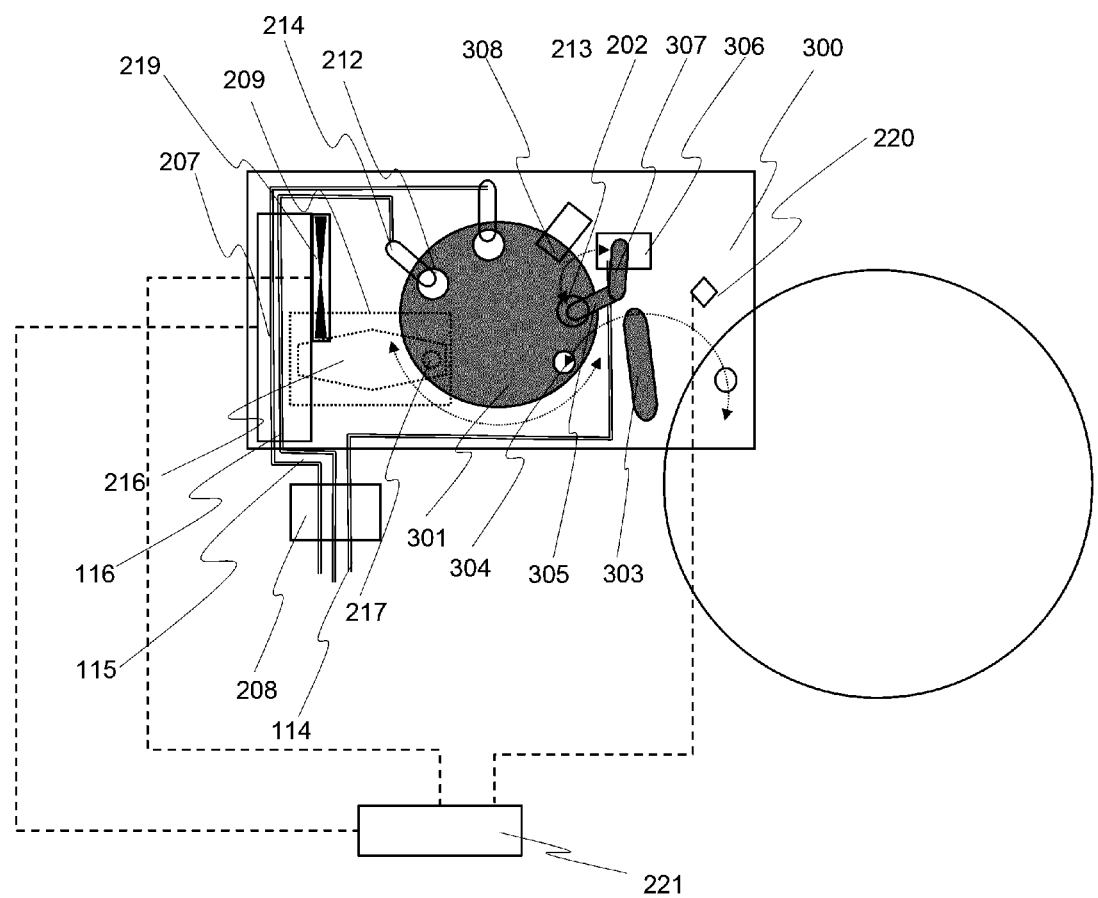

AUTOMATIC ANALYZER

TECHNICAL FIELD

The present invention relates to an automatic analyzer.

BACKGROUND ART

In the field of medical or biotechnology, there is an immune analyzer that forms an immune complex by immunologically binding magnetic microparticles with a luminescent label or the like under a constant temperature environment of an incubator (a reaction disk) for specific biological components or chemical substances contained in a sample of biological origin such as blood, serum, and urine contained in a sample, and detects the luminescent label. In order to improve detection sensitivity of a component to be detected, an analyzer that combines a flow cell type detection mechanism with a B/F separation mechanism is disclosed (see PTL 1).

CITATION LIST

Patent Literature

PTL 1: WO 2009/151058

SUMMARY OF INVENTION

Technical Problem

Since PTL 1 does not refer to making a temperature environment of the B/F separation mechanism and a detector uniform, environmental changes in a B/F separation step and the like (for example, ionic strength change due to solution replacement, and temperature change) may affect an equilibrium state of an immunological binding reaction.

Therefore, an object of the invention is to provide an automatic analyzer that prevents an effect of various environmental changes on the equilibrium state of the immunological binding reaction.

Solution to Problem

An automatic analyzer according to an aspect of the invention includes a B/F separation unit that executes a B/F separation step separating an unreacted component and a reacted component from a liquid in which a sample and a reagent are reacted, a detection unit that detects a reacted component in the liquid after the B/F separation step, and a temperature maintaining unit that maintains the B/F separation unit and the detection unit in substantially the same temperature environment.

Advantageous Effect

According to the invention, it is possible to provide an automatic analyzer that prevents an effect of various environmental changes on an equilibrium state of an immunological binding reaction.

BRIEF DESCRIPTION OF DRAWINGS

FIG. 1 is a top view of an automatic analyzer.

FIG. 2 is a top view of a B/F separation and detection mechanism of Embodiment 1.

FIG. 3 is a side view of the B/F separation and detection mechanism of Embodiment 1.

FIG. 4 is a top view of a B/F separation and detection mechanism of Embodiment 2.

DESCRIPTION OF EMBODIMENTS

Embodiments will be described below.

Embodiment 1

Hereinafter, Embodiment 1 will be described with reference to the drawings.

An automatic analyzer 100 shown in FIG. 1 includes a magazine 101 that holds a chip 121 and a reaction container 122 for dispensing a sample (specimen), a constant temperature controlled incubator 102, a reagent holding unit (a reagent disk) 103 that holds a reagent container 123 having various reagents, a first transport unit 104 that transports the chip 121 and the reaction container 122, a reagent dispensing unit 105 that dispenses a reagent to the reaction container 122, a second transport unit 106 that transports the sample, a sample dispensing unit 107 that dispenses the sample into the reaction container 122, a sample rack 108 that accommodates a sample container 124 having the sample, a first liquid container 111 that accommodates a B/F separated replacement liquid (hereinafter, a first liquid) used in a first B/F separation step of removing unreacted components from the reaction container 122 that accommodates a mixed solution of the sample and the reagent, a second liquid container 112 that accommodates a detection liquid (hereinafter, a second liquid) used in a second B/F separation step (a detection step implemented by a flow cell type detector), a cleaning liquid container 113 that accommodates a cleaning liquid used for cleaning the detector, flow paths 114, 115, and 116, each having a pressure control mechanism, a preheater 208, a B/F separation and detection mechanism 200, and the like. The first liquid container 111, the second liquid container 112, and the cleaning liquid container 113 are connected to the flow paths 114, 115, and 116 separately, and the flow paths 114, 115, and 116 are connected to the B/F separation and detection mechanism 200 via the preheater 208.

The incubator 102 is provided with reaction container installation holes for holding a plurality of reaction containers 122 on a circumference, and performs a rotation operation in order to transport the reaction containers 122 to a predetermined position, and is generally controlled at a constant temperature of 37° C. Accordingly, an immunological reaction of components contained in a solution in the reaction container 122 is promoted, and an immune complex is formed.

The reagent holding unit 103 is provided with a reagent container installation hole for holding a plurality of reagent containers 123 on a circumference, and performs a rotation operation for transporting the reagent containers 123 to a predetermined position.

The first transport unit 104 transports the reaction container 122 held in the magazine 101 to the reaction container installation holes of the incubator 102, and transports the chip 121 to a chip mounting position 109.

The reagent dispensing unit 105 includes a reagent probe that dispenses the reagent in the reagent container 123 into the reaction container 122 installed in the incubator 102. The reagent probe includes a pressure control mechanism using a syringe or the like via a flow path. The reagent dispensing unit 105 moves the reagent probe above the reagent container 123 and then lowers to immerse the reagent probe in the reagent in the reagent container 123. By the above-described pressure control, a predetermined amount of the reagent is absorbed from a tip end of the reagent probe. Thereafter, the reagent dispensing unit 105 raises the reagent probe, moves the reagent probe from above the reagent container 123 to above the incubator 102, and lowers the reagent probe to a predetermined position of the reaction container 122. By the above-described pressure control, the predetermined amount of the reagent from the tip end of the reagent probe is discharged into the reaction container 122.

The second transport unit 106 moves the plurality of sample containers 124 along a transport line (a rail) on the sample rack 108.

The sample dispensing unit 107 includes a sample probe that dispenses a sample in the sample container 124 into the reaction container 122 installed in the incubator 102. The sample probe includes a pressure control mechanism using a syringe or the like via the flow path. The sample dispensing unit 107 accesses the sample rack 108, the incubator 102, and the chip mounting position 109 by the rotation operation. The sample dispensing unit 107 moves the sample probe above the chip 121 installed in the chip mounting position 109, and then lowers the sample probe to press-fit the chip 121. Then, the sample dispensing unit 107 raises the sample probe, moves the sample probe above the sample rack 108 by the rotation operation, and then lowers to immerse the chip 121 mounted on the sample probe in the sample container 124. By the above-described pressure control, a predetermined amount of the sample is absorbed from a tip end of the sample probe. Thereafter, the sample dispensing unit 107 raises the sample probe, moves the sample probe from above the sample rack 108 to above the incubator 102, and lowers the sample probe to the position of the predetermined reaction container 122. By the above-described pressure control, the predetermined amount of the sample from the tip end of the sample probe is discharged into the reaction container 122.

In this way, the reaction container 122 to which the predetermined amount of the reagent and the sample are discharged is held for a predetermined time on the incubator 102 controlled to a predetermined temperature. Accordingly, an immune reaction of antibody components, luminescent labels, and magnetic microparticles contained in the reagent and a measurement target contained in the sample is promoted, and an immune complex is formed.

Next, FIGS. 2 and 3 show the B/F separation and detection mechanism 200 in which a B/F separation mechanism and a detection mechanism are integrally accommodated.

The B/F separation and detection mechanism 200 includes a reaction container transport unit 201 that transports the reaction container 122 holding the immune complex from the incubator 102 into the B/F separation and detection mechanism 200, a temperature maintaining unit 230, a B/F separation unit 240 that executes a B/F separation step of separating unreacted components and reactive components from the liquid in which the sample and the reagent are reacted, a detection unit 209 that detects reactive components in the liquid after the B/F separation step, a detection unit container transport unit 210, a temperature sensor 220, a control unit 221, a cover 225 and the like.

The cover 225 covers the entire B/F separation and detection mechanism 200 in order to separate a space inside the B/F separation and detection mechanism 200 (hereinafter, an internal space) from the outside. In addition, the cover 225 includes a notch-shaped gap 218 that connects the B/F separation and detection mechanism 200 with an external space. The reaction container transport unit 201 accesses the reaction container 122 on the incubator 102 via the gap 218. The gap 218 minimizes heat inflow and outflow by setting a minimum opening area necessary for transporting the reaction container 122.

The temperature maintaining unit 230 maintains the B/F separation unit 240 and the detection unit 209 in substantially the same temperature environment, and includes a temperature control unit 207 having a cool and heat source such as a Peltier element for maintaining the internal space at a constant temperature, and one or more fans 219 for circulating air in the internal space. The fan 219 is arranged to promote efficient air convection for maintaining an atmosphere in the internal space at a more uniform temperature. For example, the fan 219 is installed near the cool and heat source of the temperature control unit 207, and air near the cool and heat source is blown toward a far part in the internal space, that is, toward the incubator 102 direction.

The control unit 221 controls an output of the temperature control unit 207 and the fan 219 such that each mechanism and the atmosphere temperature in the space are maintained at a predetermined temperature based on information of the one or more temperature sensors 220.

The preheater 208 has an auxiliary function for maintaining each solution near a target temperature before the solution passing through the flow paths 114, 115, and 116 flows into the B/F separation and detection mechanism 200. The preheater 208 includes a temperature-controlled metal flow path and atmosphere inside the preheater 208. The temperature of the solution in the flow paths 114, 115, and 116 passing through the inside of the preheater 208 is controlled by exchanging heat therewith. The preheater 208 includes a cool and heat source such as a Peltier element and a sensor for measuring a temperature near the flow paths inside, and controls the cool and heat source such as the Peltier element based on temperature information measured by the sensor.

A part or all of the flow paths 114, 115, and 116 flowing into the B/F separation and detection mechanism 200 passes through the inside of the temperature control unit 207, and controls the solution inside the flow paths to a target temperature, similarly to the preheater 208. The flow paths passing through the inside of the temperature control unit 207 is further subjected to heat exchange with the atmosphere controlled to the target temperature in the internal space, and thus the flow paths are maintained at the same temperature as each mechanism and the atmosphere in the B/F separation and detection mechanism 200.

When the temperature control unit 207 and the preheater 208 are combined, the temperature control can be more efficiently performed, and a configuration including only one of the temperature control unit 207 and the preheater 208 may be used. Further, although the configuration in which the flow paths 115 and 116 passing through the inside of the temperature control unit 207 is illustrated, temperature control may be performed only by heat exchange with the atmosphere controlled to the target temperature in the B/F separation and detection mechanism 200 without passing through the temperature control unit 207 as the flow path 114. However, when the flow path does not pass through the temperature control unit 207, it is desirable to pass through the preheater 208.

The reaction container transport unit 201 transports the reaction container 122 from above the incubator 102 to the B/F separation and detection mechanism 200 and transports the reaction container 122 to the B/F separation unit 240.

The B/F separation unit 240 includes a magnetic collecting unit 202 that has a permanent magnet or an electromagnet and magnetically collects magnetic particles contained in the reaction container 122 to an inner wall of the container, a reaction liquid absorption unit 203 that absorbs a solution in the reaction container 122, a first liquid discharge unit 204 that discharges a first liquid to the reaction container 122, a cleaning tank 205, and a stirring unit stirring the solution in the reaction container 122.

The reaction liquid absorption unit 203 rotates and moves above the reaction container 122 installed in the magnetic collecting unit 202 and then lowers to immerse an absorption probe provided in the reaction liquid absorption unit 203 in the solution in the reaction container 122. The absorption probe includes a pressure control mechanism using a syringe or the like via the flow path, the pressure control allows the solution in the reaction container 122 to be absorbed from a tip end of the absorption probe, and, instead of absorbing the immune complexes and magnetic particles collected on the inner wall of the reaction container 122, only components unnecessary for the detection of the sample containing unreacted substances, impurities and the like are absorbed. The reaction liquid absorption unit 203 rotates and moves above the cleaning tank 205 and then lowers to discharge the solution absorbed from the tip end of the absorption probe by the above-described pressure control into the cleaning tank 205, and washes the tip end of the absorption probe with running water in the cleaning tank 205 by washing water.

Then, the first liquid discharge unit 204 rotates and moves above the reaction container 122 installed in the magnetic collecting unit 202 and then lowers downward. A discharge probe provided in the first liquid discharge unit 204 communicates with a pressure control mechanism using the first liquid container 111 that holds the first liquid via the flow path 114, a syringe and the like. By the pressure control, the first liquid in the first liquid container 111 is absorbed into the flow path, and a predetermined amount of the first liquid is discharged into the reaction container 122 from the discharge probe. The first liquid is maintained at the same temperature as each mechanism and the atmosphere in the internal space by heat exchange in the preheater 208 and the B/F separation and detection mechanism 200. As the first liquid, a buffer solution having a low salt concentration is generally used.

The reaction container 122 from which the first liquid is discharged is transported by the reaction container transport unit 201 and is installed in a stirring unit 206. The stirring unit 206 stirs the solution in the reaction container 122 by, for example, a supersonic oscillation mechanism or the like that gives a rotation movement, an oscillatory movement, or a convective movement to the solution in the reaction container, and disperses the magnetic particles collected on the inner wall of the container in the first liquid. In this way, unreacted components containing impurities or the like derived from the sample are removed from the reaction container 122, and a reaction liquid formed of only the magnetic particles including the immune complex remains in the reaction container 122.

The reaction container 122 holding the reaction liquid is transported by the reaction container transport unit 201, and is installed in a reaction container holding unit 211 of the detection unit container transport unit 210 located below the detection unit 209. The detection unit container transport unit 210 includes a second liquid container 212 in which a second liquid is stored and a cleaning liquid container 213 in which the cleaning liquid is stored. The detection is performed by a flow cell type detector 216.

A second liquid supply nozzle 214 is connected to a pressure control mechanism using a second liquid container 112 that holds the second liquid and a syringe via the flow path 115. By the pressure control, the second liquid in the second liquid container 112 is absorbed into the flow path, and a predetermined amount of the second liquid is discharged from the second liquid supply nozzle 214 into the second liquid container 212. Similarly, a cleaning liquid supply nozzle 215 is connected to a pressure control mechanism using a cleaning liquid container 113 that holds the cleaning liquid and a syringe via the flow path 116. By the pressure control, the cleaning liquid in the cleaning liquid container 113 is absorbed into the flow path, and a predetermined amount of the cleaning liquid is discharged from the cleaning liquid supply nozzle 215 into the cleaning liquid container 213. The flow path 115 of the second liquid and the flow path 116 of the cleaning liquid are maintained at the same temperature as each mechanism and the atmosphere in the internal space by heat exchange when the flow path 115 of the second liquid and the flow path 116 of the cleaning liquid pass through the preheater 208, the temperature control unit 207 and the B/F separation and detection mechanism 200.

The detection unit container transport unit 210 lowers, rotates, and raises a detection nozzle 217 connected to the detector 216 in the detection unit 209, and immerses a tip end of the detection nozzle 217 in the reaction liquid in the reaction container 122. The detection nozzle 217 is connected to a pressure control mechanism using a syringe or the like via a flow path 226. By the pressure control, a predetermined amount of the reaction liquid in the reaction container 122 is absorbed into the detection nozzle 217, and is sent to the detector 216.

The detector 216 is provided so as to be partially in contact with the temperature control unit 207, and is maintained at the same temperature as each mechanism and the atmosphere in the B/F separation and detection mechanism 200 by heat exchange with the atmosphere in the temperature control unit 207 and the B/F separation and detection mechanism 200. Alternatively, as a structure for more efficiently controlling the temperature of the detector 216, a detector temperature control unit using a cool and heat source such as a Peltier element that controls the temperature of only the detector 216, a detector temperature sensor for measuring the temperature inside or near the detector, and a detector temperature control unit for feedback and control of information of the temperature sensor may be added. In this case, the detector 216 and the temperature control unit 207 are arranged to promote more efficient heat exchange. It is more efficient when an area of a contact surface between the detector 216 and the temperature control unit 207 or thermal conductivity is taken into consideration.

In the reaction liquid sent to the detector 216, only the magnetic particles containing the immune complex in the reaction liquid are magnetically captured in a detection region 222 inside the detector 216. In order to magnetically capture the magnetic particles in the detection region, a magnetic particle capturing magnet 223 is provided at a lower part of the detection region 222 by up-down driving, and the magnetic particle capturing magnet 223 is brought close to the lower part of the detection region of the detector 216 during capture.

Next, the detection unit container transport unit 210 lowers, rotates, and raises the detection nozzle 217 connected to the detector 216, and immerses the tip end of the detection nozzle 217 in the solution of the second liquid container 212. By the above-described pressure control, a predetermined amount of the second liquid is absorbed by the detection nozzle 217, and is sent to the detector 216.

The second liquid is used to detect a labeling substance contained in the immune complex and quantify a measurement target, and fills the detection region inside the detector 216 where the magnetic particles containing the immune complex are magnetically captured. As a method of detecting the labeling substance, for example, there is a method based on electrochemiluminescence or chemiluminescence, in which the second liquid and the labeling substance suitable for each, a structure and physical properties of the detection region are selected, and an amount of luminescence resulting from a luminescence reaction of the labeling substance is measured using a photomultiplier tube 224 as a detector.

Next, the detection unit container transport unit 210 lowers, rotates, and raises the detection nozzle 217 connected to the detector 216, and immerses the tip end of the detection nozzle 217 in the solution of the cleaning liquid container 213. By the above-described pressure control, a predetermined amount of the cleaning liquid in the cleaning liquid container 213 is absorbed by the detection nozzle 217, and is sent to the detector 216. At this time, the magnetic particle capturing magnet 223, which is brought close to the detection region to magnetically capture the magnetic particles, is separated from the lower part of the detection region 222 of the detector 216. The cleaning liquid cleans the detection region by removing the magnetic particles including the immune complex and the second liquid. Accordingly, the detector 216 is provided for the next measurement.

Embodiment 2

The B/F separation and detection mechanism of Embodiment 2 is shown in FIG. 4. Differences between Embodiment 1 and Embodiment 2 will be described below.

The detection unit container transport unit 301 of Embodiment 2 includes the B/F separation unit 240 at a lower part on a rotation orbit thereof. The reaction container 122 is transported from the incubator 102 to the reaction container holding unit 304 of the detection container transport unit 301 by rotating and un-down driving the reaction container transport unit 303, and the reaction container 122 is transported to an upper part of the B/F separation unit 240 by the rotation operation of the detection unit container transport unit 301, and is installed in the magnetic collecting unit 202 by a lowering operation. The subsequent steps are the same as in Embodiment 1.

When Embodiment 2 is compared with Embodiment 1, it is possible to save space in a separated space including the B/F separation and detection mechanism and the mechanisms, thereby simplifying the temperature control mechanism and increasing the accuracy. However, when operation cycle time related to processing capability of the analyzer is short, a temporal limitation of the mechanism operation occurs. Therefore, Embodiment 2 is more suitable for, for example, an apparatus having low analysis processing capability and a small analyzer size.

REFERENCE SIGN LIST 100 automatic analyzer
101 magazine
102 incubator
103 reagent holding unit
104 first transport unit
105 reagent dispensing unit
106 second transport unit
107 sample dispensing unit
108 sample rack
111 first liquid container
112 second liquid container
113 cleaning liquid container
114 first liquid flow path
115 second liquid flow path
116 cleaning liquid flow path
200 B/F separation and detection mechanism

The invention claimed is:

1. An automatic analyzer comprising:
   a first liquid container holding a first liquid;
   a B/F separation unit that executes B/F separation of separating an unreacted component and a reacted component from a liquid in which a sample and a reagent are reacted;
   a detection unit that detects a reacted component in the liquid after the B/F separation; and
   a temperature maintaining unit that maintains the B/F separation unit and the detection unit in substantially the same temperature environment,
   a cover that encloses the B/F separation unit, the detection unit and the temperature maintaining unit within the cover,
   wherein the B/F separation unit includes:
   a magnetism collecting unit that collects magnetic microparticles in the solution,
   an absorption nozzle that absorbs unnecessary components from a reaction container,
   a discharge nozzle that discharges the first liquid for generating a reaction liquid into the reaction container, and
   a stirring unit that generates the reaction liquid by stirring a component not absorbed by the absorption nozzle and the first liquid in the reaction container, and
   wherein the detection unit includes a detector with a cell through which reaction liquid flows, the detector causing the reaction liquid to emit light and detects the light emitted from the reaction liquid.

2. The automatic analyzer according to claim 1, further comprising:
   a transport unit disposed within the cover,
   wherein the cover includes a qap through which the transport unit is configured to transport a reaction container into the cover and to the B/F separation unit.

3. The automatic analyzer according to claim 1, further comprising:
   a second liquid container disposed outside of the cover and the cover that holds a second liquid;
   a third liquid container disposed outside of the cover and the cover that holds a third liquid; and
   a detection unit container transport unit, disposed below the detection unit, including a reaction container that stores the reaction liquid, a third liquid container that stores the second liquid, and a fourth liquid container that stores the third liquid.

4. The automatic analyzer according to claim 3, wherein the reaction container is arranged in a lower part of the B/F separation unit.

5. The automatic analyzer according to claim 1, wherein the temperature maintaining unit includes a cold and heat source using a Peltier element, a blower for air circulation, and a sensor for measuring a part or a plurality of points of the temperature in the internal space.

6. The automatic analyzer according to claim 2, further comprising:
- a second liquid container disposed outside of the cover that holds a second liquid;
- a third liquid container disposed outside of the cover that holds a third liquid; and
- a detection unit container transport unit, disposed below the detection unit, including a reaction container that stores the reaction liquid, a third liquid container that stores the second liquid, and a fourth liquid container that stores the third liquid,
- wherein the transport unit is configured to transport the reaction container from the B/F separation unit to the detection unit container transport unit.

7. The automatic analyzer according to claim 1, further comprising:
- a pre-heater having a temperature-controlled metal flow path disposed outside of the cover,
- wherein the first liquid container and the discharge nozzle of the B/F separation unit are connected via a first flow path through which the first liquid flows, and
- wherein the first flow path is disposed within the pre-heater and within the cover.

* * * * *